(12) United States Patent
Tamada

(10) Patent No.: US 9,456,804 B2
(45) Date of Patent: Oct. 4, 2016

(54) ULTRASOUND MEASUREMENT APPARATUS AND ULTRASOUND MEASUREMENT METHOD

(71) Applicant: SEIKO EPSON CORPORATION, Tokyo (JP)

(72) Inventor: Natsumi Tamada, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 87 days.

(21) Appl. No.: 14/281,067

(22) Filed: May 19, 2014

(65) Prior Publication Data

US 2014/0357992 A1    Dec. 4, 2014

(30) Foreign Application Priority Data

Jun. 4, 2013   (JP) .................................. 2013-117620

(51) Int. Cl.
  *A61B 8/00*  (2006.01)
  *A61B 8/08*  (2006.01)
  *A61B 8/06*  (2006.01)

(52) U.S. Cl.
  CPC .............. *A61B 8/5223* (2013.01); *A61B 8/06* (2013.01); *A61B 8/0891* (2013.01); *A61B 8/488* (2013.01); *A61B 8/4218* (2013.01); *A61B 8/4405* (2013.01); *A61B 8/469* (2013.01); *A61B 8/543* (2013.01)

(58) Field of Classification Search
  CPC .. A61B 5/02007; A61B 5/022; A61B 5/489; A61B 5/721; A61B 8/5223; A61B 2019/461; A61B 8/0891; A61B 8/06; A61B 8/488; A61B 8/4218; A61B 8/4405; A61B 8/469; A61B 8/543; G01S 15/8979; G01S 15/8984; G01S 7/52036; G01S 7/52042; G06T 2207/10132; G06T 2207/30101; G06T 7/0085

See application file for complete search history.

(56) References Cited

U.S. PATENT DOCUMENTS

| | | | | |
|---|---|---|---|---|
| 4,630,612 A | * | 12/1986 | Uchida | A61B 8/06 600/441 |
| 5,409,010 A | * | 4/1995 | Beach | A61B 8/06 600/455 |
| 6,023,968 A | * | 2/2000 | Spratt | G01F 1/663 73/204.14 |
| 2014/0343431 A1 | * | 11/2014 | Vajinepalli | A61B 8/06 600/454 |

FOREIGN PATENT DOCUMENTS

| | | |
|---|---|---|
| JP | A-2007-222291 | 9/2007 |
| JP | A-2008-173177 | 7/2008 |
| JP | A-2013-169270 | 9/2013 |
| WO | WO 2013/125094 A1 | 8/2013 |

* cited by examiner

*Primary Examiner* — Elmer Chao
(74) *Attorney, Agent, or Firm* — Oliff PLC

(57) ABSTRACT

A region of interest which is considered to be a vascular wall of an artery is set in a B-mode image, and tracking processing is performed for each region of interest. A maximum displacement velocity Vu in a positive direction and a maximum displacement velocity Vd in a negative direction are obtained as a peak value of a displacement velocity of the vascular wall. If a first peak ratio (Vu/Vd) of a region of interest corresponding to an anterior wall is equal to or greater than a predetermined first feature threshold value (for example, 2.0) using the obtained maximum displacement velocity Vu in the positive direction and maximum displacement velocity Vd in the negative direction, it is determined that the region of interest is an artery.

8 Claims, 12 Drawing Sheets

[DISPLACEMENT VELOCITY]

[FIRST PEAK RATIO: MAXIMUM VELOCITY Vu IN POSITIVE DIRECTION/MAXIMUM VELOCITY Vd IN NEGATIVE DIRECTION]

[SECOND PEAK RATIO: MAXIMUM VELOCITY Vd IN NEGATIVE DIRECTION/MAXIMUM VELOCITY Vu IN POSITIVE DIRECTION]

ULTRASOUND MEASUREMENT APPARATUS AND ULTRASOUND MEASUREMENT METHOD

BACKGROUND

1. Technical Field

The present invention relates to an ultrasound measurement apparatus which measures a biological tissue by ultrasound measurement, or the like.

2. Related Art

Biological information in a body is measured by an ultrasound measurement apparatus to evaluate a vascular function or to diagnose a vascular disease.

For example, as one of the biological information, the IMT (Intima Media Thickness) of a carotid artery as an index of arteriosclerosis is measured. During the measurement relating to the IMT or the like, the carotid artery needs to be found and a measurement point needs to be appropriately determined. Normally, an operator applies an ultrasound probe over the neck, finds the carotid artery to be measured while viewing a B-mode image displayed on a monitor, and manually sets the found carotid artery as a measurement point.

In the related art, although a lot of skill to promptly execute a sequence of measurement operations and to appropriately find a carotid artery is required, in recent years, a function which supports the measurement operations has been devised. For example, JP-A-2008-173177 discloses a method which automatically detects a vascular wall using reflected wave signal strength from a biological tissue obtained by processing amplitude information of a received reflected wave and the moving velocity of the biological tissue obtained by processing phase information of the received reflected wave. Specifically, the boundary of the vascular wall and the blood flow region is detected based on a first finding that "the strength of the reflected wave signal in the blood flow region of the blood vessel extremely decreases compared to the strength of the reflected wave signal in the vascular wall" and a second finding that "the moving velocity calculated from the phase information of the reflected wave signal is fast in the blood flow region and is slow in the vascular wall".

However, in the detection method disclosed in JP-A-2008-173177, while a blood vessel can be detected, it is not possible to determine whether the blood vessel is an artery or a vein.

In general, since an artery should be accompanied by pulsation and a vein should not be accompanied by pulsation, it is carelessly considered that an artery and a vein can be identified according to the presence/absence of pulsation. However, in a vascular region, such as an internal jugular vein, which is comparatively close to the heart, right atrial contraction and ventricular contraction may propagate and even a vein may be accompanied by pulsation. For this reason, accurate identification merely based on the presence/absence of pulsation may be difficult.

SUMMARY

An advantage of some aspects of the invention is to realize a technique for identifying an artery and a vein.

A first aspect of the invention is directed to an ultrasound measurement apparatus including a vascular wall tracking unit which tracks the position of a vascular wall of a blood vessel in a biological tissue on the basis of a reflected wave signal of an ultrasonic wave radiated toward the biological tissue, a determination unit which determines whether or not the blood vessel to be tracked is an artery on the basis of whether or not positional change of the vascular wall to be tracked is positional change of a vascular wall of an artery, and a report unit which reports the determination result of the determination unit.

As another aspect, the aspect of the invention can be configured as an ultrasound measurement method including tracking the position of a vascular wall of a blood vessel in a biological tissue on the basis of a reflected wave signal of an ultrasonic wave radiated toward the biological tissue, determining whether or not the blood vessel to be tracked is an artery on the basis of whether or not positional change of the vascular wall to be tracked is positional change of a vascular wall of an artery, and reporting the determination result.

According to the first and the other aspect of the invention, it is possible to track the position of the vascular wall every moment using ultrasonic waves to measure the positional change. Then, it is possible to determine whether or not the blood vessel to be tracked is an artery on the basis of whether or not the measured positional change is positional change of a vascular wall of an artery.

A second aspect of the invention is directed to the ultrasound measurement apparatus according to the first aspect of the invention, wherein the determination unit performs the determination using the relative relationship between a displacement velocity in a positive direction and a displacement velocity in a negative direction of the vascular wall.

According to the second aspect of the invention, it is possible to determine whether or not the blood vessel to be tracked is an artery on the basis of the relative relationship between the displacement velocity in the positive direction (for example, a direction to come close to an ultrasound probe) and the displacement velocity in the negative direction (for example, a direction to be separated from the ultrasound probe) of the vascular wall.

A third aspect of the invention is directed to the ultrasound measurement apparatus according to the second aspect of the invention, wherein the determination unit performs the determination using the ratio of the displacement velocity in the positive direction to the displacement velocity in the negative direction and the ratio of the displacement velocity in the negative direction to the displacement velocity in the positive direction.

According to the third aspect of the invention, it is possible to determine whether or not the blood vessel to be tracked is an artery using the ratio of the displacement velocity in the negative direction and the displacement velocity in the positive direction. This is because, if the blood vessel to be tracked is an artery, features are represented by the ratio of the displacement velocity in the positive direction to the displacement velocity in the negative direction and the ratio of the displacement velocity in the negative direction to the displacement velocity in the positive direction.

A fourth aspect of the invention is directed to the ultrasound measurement apparatus according to the second or third aspect of the invention, wherein the determination unit determines that the blood vessel to be tracked is not an artery when the ratio of the displacement velocity in the positive direction to the displacement velocity in the negative direction and the ratio of the displacement velocity in the negative direction to the displacement velocity in the positive direction satisfy a predetermined almost equal condition.

According to the fourth aspect of the invention, if the displacement velocity in the negative direction and the displacement velocity in the positive direction are almost equal, it can be determined that the blood vessel to be tracked is not an artery.

A fifth aspect of the invention is directed to the ultrasound measurement apparatus according to any of the first to fourth aspects of the invention, wherein the determination unit performs the determination using the condition for an anterior vascular wall when the vascular wall is an anterior vascular wall and performs the determination using a condition for a posterior vascular wall when the vascular wall is a posterior vascular wall.

According to the fifth aspect of the invention, it becomes possible to perform more appropriate determination by selecting a criterion for determination to be applied according to whether or not the blood vessel to be tracked is an anterior wall or a posterior wall.

A sixth aspect of the invention is directed to the ultrasound measurement apparatus according to any of the first to fifth aspects of the invention, wherein the determination unit performs the determination using the peak waveform of a displacement velocity of the vascular wall.

According to the sixth aspect of the invention, it is possible to determine whether or not the blood vessel to be tracked is an artery on the basis of the peak waveform of the displacement velocity.

BRIEF DESCRIPTION OF THE DRAWINGS

The invention will be described with reference to the accompanying drawings, wherein like numbers reference like elements.

FIG. 2A is a graph of an arterial vessel diameter, and FIG. 2B is a graph of a venous vessel diameter.

FIG. 3A is a displacement velocity graph relating to an artery, FIG. 3B is a diagram showing an example of a first peak ratio, and FIG. 3C is a diagram showing an example of a second peak ratio.

FIG. 4A is a displacement velocity graph relating to a vein, FIG. 4B is a diagram showing an example of a first peak ratio, and FIG. 4C is a diagram showing an example of a second peak ratio.

DESCRIPTION OF EXEMPLARY EMBODIMENTS

Figure 1:
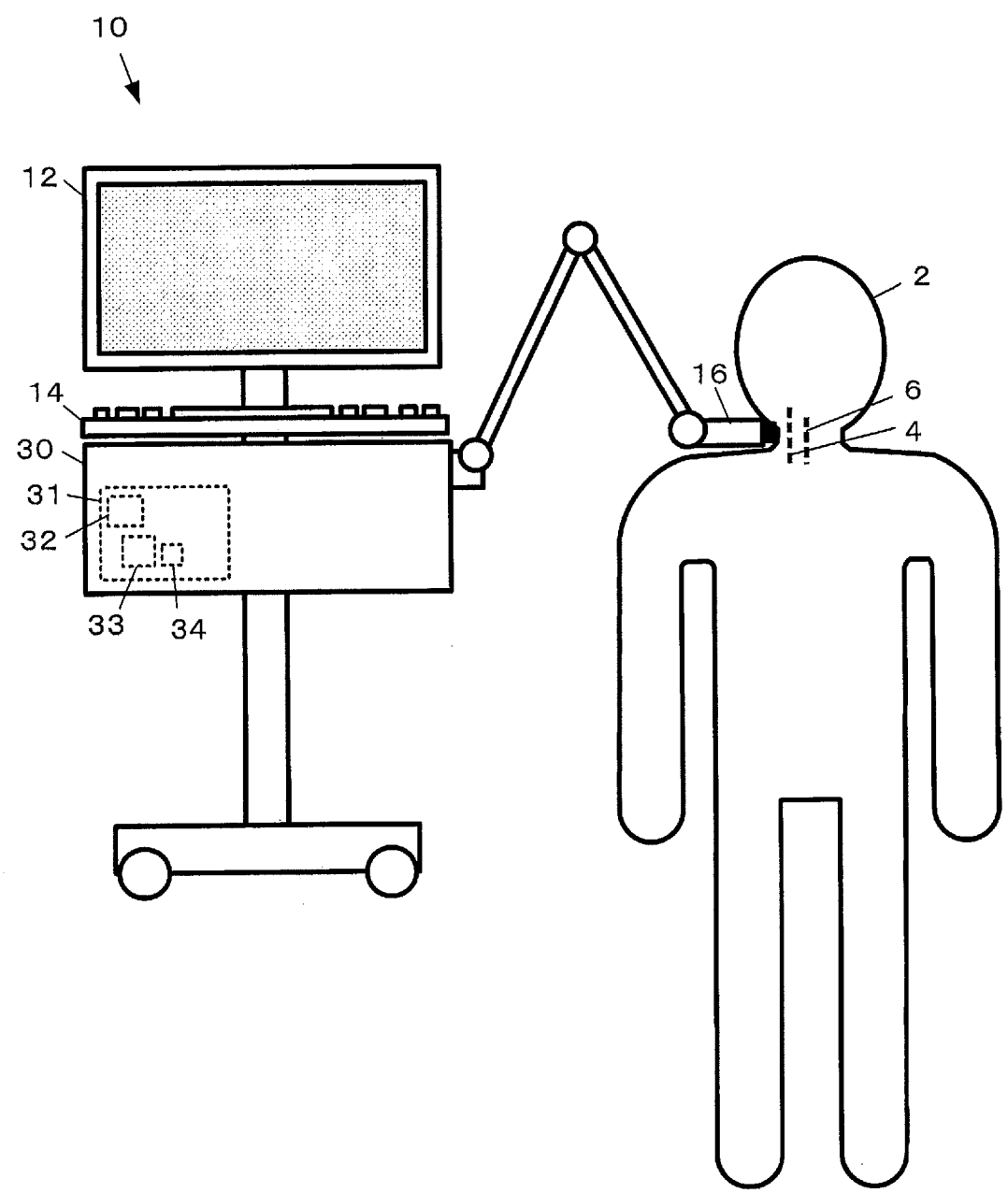
FIG. 1 is a diagram showing a system configuration example of a biological information measurement apparatus.

FIG. 1 is a diagram showing a system configuration example of an ultrasound measurement apparatus 10 in this embodiment. The ultrasound measurement apparatus 10 is an apparatus which measures reflected waves of ultrasonic waves to measure biological information of a subject 2. In this embodiment, an artery 4 and a vein 6 are automatically identified, and the IMT (Intima Media Thickness) of the artery 4 is calculated as one of biological information.

The ultrasound measurement apparatus 10 includes a touch panel 12 which serves both as means for displaying a measurement result or operation information in the form of images and means for operation input, a keyboard 14 for operation input, an ultrasound probe 16, and a processing device 30. A control board 31 is mounted in the processing device 30, and is connected to perform signal transmission and reception with the respective units, such as the touch panel 12, the keyboard 14, the ultrasound probe 16, and the like.

On the control board 31, in addition to a CPU 32, an ASIC, and various LSIs, a storage medium 33, such as an IC memory or a hard disk, and a communication IC 34 which realizes data communication with an external apparatus are mounted. The processing device 30 executes a measurement program stored in the storage medium 33 on the CPU 32 or the like, and realizes various functions according to this embodiment, such as artery and vein identification, calculation of the IMT of the identified artery, and image display control of the measurement result, including ultrasound measurement.

Specifically, the ultrasound measurement apparatus transmits and radiates an ultrasonic pulse from the ultrasound probe 16 toward the subject 2 under the control of the processing device 30, and receives a reflected wave thereof. The received reflected wave is amplified and subjected to signal processing, thereby generating reflected wave data, such as positional information of a biological structure of the subject 2 or time-dependent change. Reflected wave data includes images of respective modes of so-called A mode, B mode, M mode, and color Doppler. Measurement using ultrasonic waves is repeatedly executed in a predetermined cycle. A unit of measurement is called "frame".

The ultrasound measurement apparatus 10 sets a region of interest (tracking point) in a reflected wave data as a reference, and can thus perform so-called "tracking" for tracing each region of interest between different frames and calculating displacement.

The ultrasound measurement apparatus 10 identifies an artery or a vein on the basis of reflected wave data obtained by ultrasound measurement and the positional change of the region of interest acquired by tracking. That is, an artery is identified. Then, the position (including the position of each layer of a vascular wall of the artery) of the identified artery can be specified, and ultrasound measurement can be executed for the specified artery to calculate the IMT.

Description of Principle

Next, a principle of identifying an artery and a vein will be described.

Figure 2A:
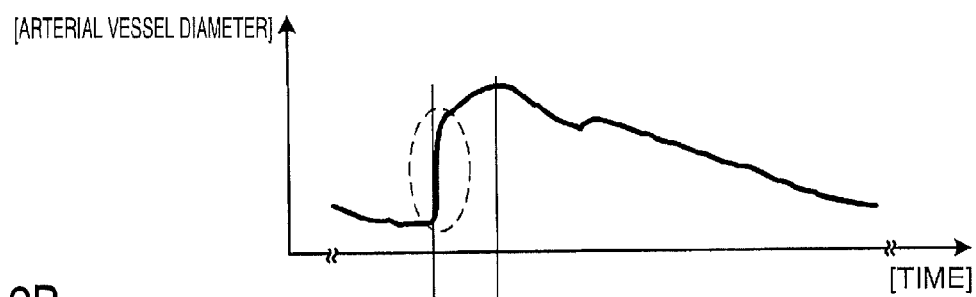
FIGS. 2A and 2B are graphs showing a change example of a vascular diameter for approximately one beat of a cardiac cycle.
Figure 2B:
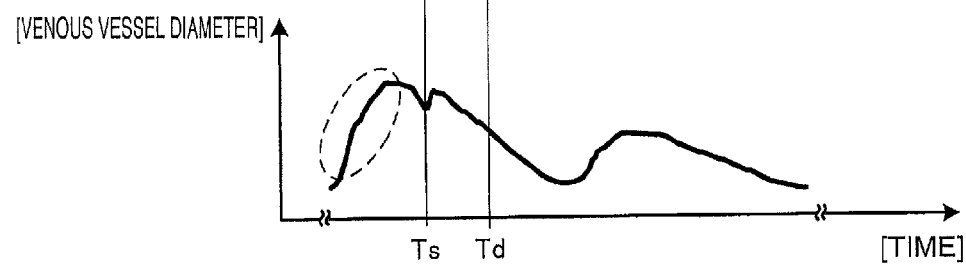

FIGS. 2A and 2B are graphs showing a change example of a vascular diameter for approximately one beat of a cardiac cycle, FIG. 2A is a graph of an arterial vessel diameter, and FIG. 2B is a graph of a venous vessel diameter.

A vascular wall (arterial wall) of an artery has a structure in which stretchability and elasticity are abundant so as to endure a pulsating blood flow flowing from the heart and a blood pressure. For this reason, the blood vessel is rapidly swollen from systole (Ts) with the pulsation of the heart and returns to the original size slowly from diastole (Td). Accordingly, since the graph of the arterial vessel diameter rises sharply since the vascular diameter increases rapidly immediately after systole (Ts) (for example, a portion enclosed by a broken line in FIG. 2A). On the other hand, the graph falls gradually since the vascular diameter decreases slowly after diastole (Td). In this way, in case of an artery, the degree of change in a thickening direction of the vascular diameter is greater than the degree of change in a thinning direction, and the difference is conspicuous.

A vascular wall (venous wall) of a vein is thin and lacking in elasticity compared to an arterial wall. A blood pressure applied to the venous wall is lower than the blood pressure applied to the arterial wall. Accordingly, in case of a vein, when comparing the degree of change of rising (a portion enclosed by a broken line in FIG. 2B) of the graph in a thickening direction of the vascular diameter with the degree of change of falling of the graph in a thinning direction, the difference as great as an artery does not appear.

In this embodiment, an artery and a vein are identified with the difference in displacement of the vascular wall accompanied with the pulsation of the artery and the vein, specifically, the difference in displacement velocity, and the position of the artery including the position of the vascular wall is detected.

FIGS. 3A to 3C and 4A to 4C are diagrams illustrating an example of a specific method of identifying an artery and a vein. The former relates to an artery, and the latter relates to a vein.

Figure 3A:
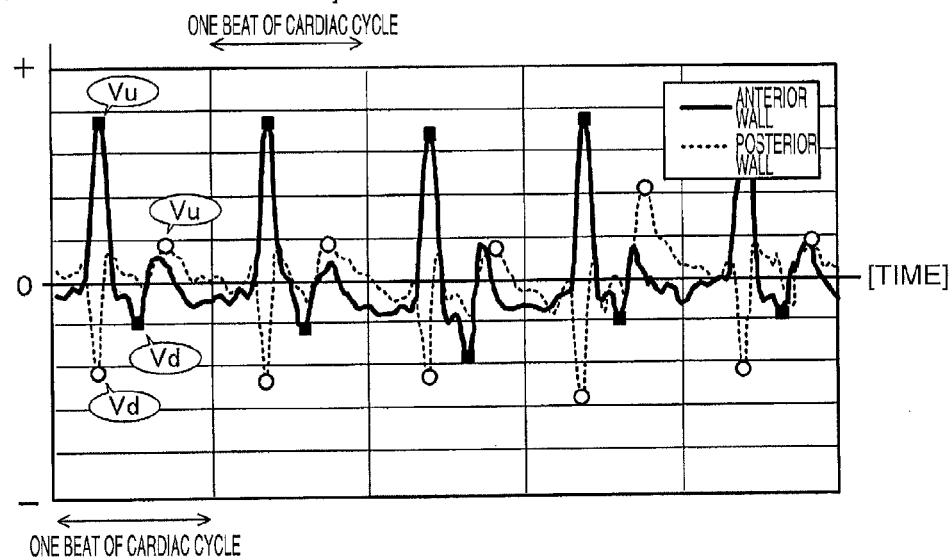
FIGS. 3A to 3C are diagrams illustrating an example of a specific method of identifying an artery and a vein.
Figure 4A:
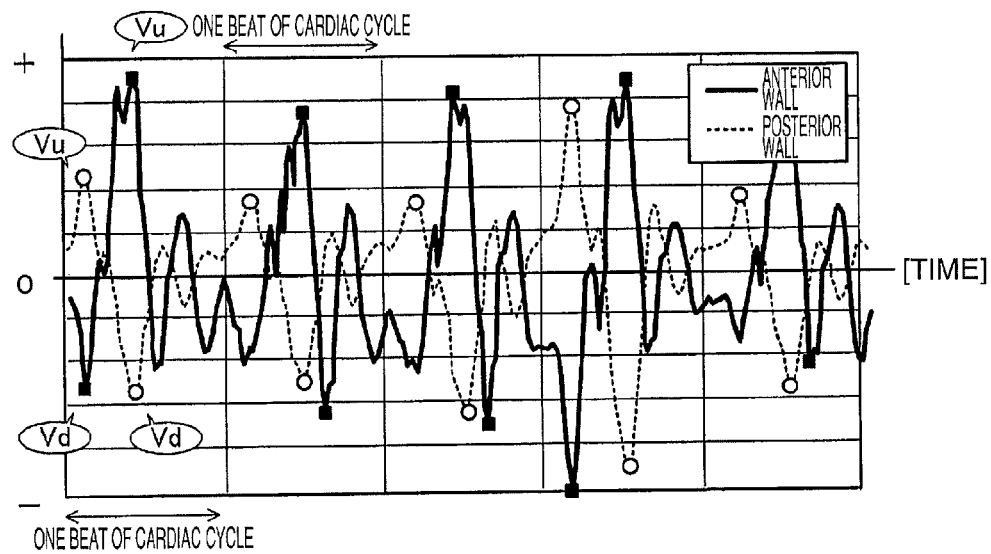
FIGS. 4A to 4C are diagrams illustrating an example of a specific method of identifying an artery and a vein.

FIGS. 3A and 4A are graphs in which the horizontal axis represents "time" and the vertical axis represents "displacement velocity", and show displacement velocity waveforms for five beats of a cardiac cycle of an anterior wall (a wall portion close to the ultrasound probe 16) and a posterior wall (a wall portion separated from the ultrasound probe 16) of a vascular wall. A solid line indicates a displacement velocity waveform of an anterior wall, and a broken line indicates a displacement velocity waveform of a posterior wall. A displacement velocity waveform is obtained, for example, using a function of tracking processing. Specifically, a region of interest is set in a B-mode image, whereby a displacement velocity relating to a region of interest can be obtained by tracking processing.

"+ (plus)" of the horizontal axis "displacement velocity" represents displacement in a direction (positive direction) to come close to the ultrasound probe 16, and "− (minus)" represents displacement in a direction (negative direction) to be separated from the ultrasound probe 16.

Each black square plot on the waveform represents the peak of the anterior wall at each beat of the cardiac cycle, and each white circular plot represents the peak of the posterior wall.

The vascular wall of the artery and the vascular wall of the vein repeat displacement motion while moving in the plus direction and the minus direction.

Here, the ratio of "the maximum displacement velocity Vu in the positive direction" and "the maximum displacement velocity Vd in the negative direction" at one beat of the cardiac cycle is obtained as an index value representing the degree of change of the vascular diameter.

A first index value is a "first peak ratio" when a numerator is the maximum displacement velocity Vu in the positive direction and a denominator is the maximum displacement velocity Vd in the negative direction. The first peak ratio may also be referred to as the maximum displacement velocity Vu in the positive direction to the maximum displacement velocity Vd in the negative direction. The graphs of FIGS. 3B and 4B show the first peak ratio of each cardiac cycle, a black square plot represents the first peak ratio of the anterior wall, and a white circular plot represents the first peak ratio of the posterior wall.

A second index value is a "second peak ratio" when a numerator is the maximum displacement velocity Vd in the negative direction and a denominator is the maximum displacement velocity Vu in the positive direction. The second peak ratio may be also referred to as the maximum displacement velocity Vd in the negative direction to the maximum displacement velocity Vu in the positive direction. The graphs of FIGS. 3C and 4C show the second peak ratio of each cardiac cycle, a black square plot represents the second peak ratio of the anterior wall, and a white circular plot represents the second peak ratio of the posterior wall.

Figure 3B:
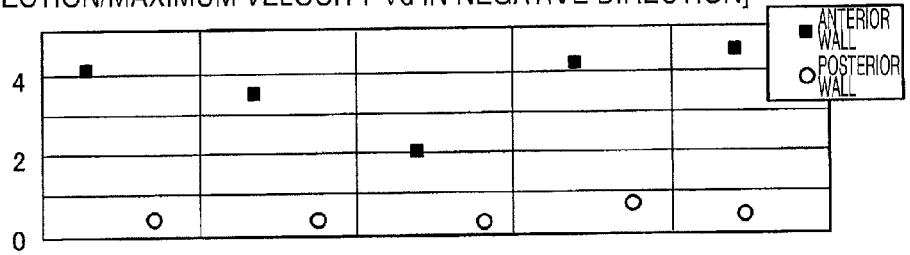
Figure 3C:
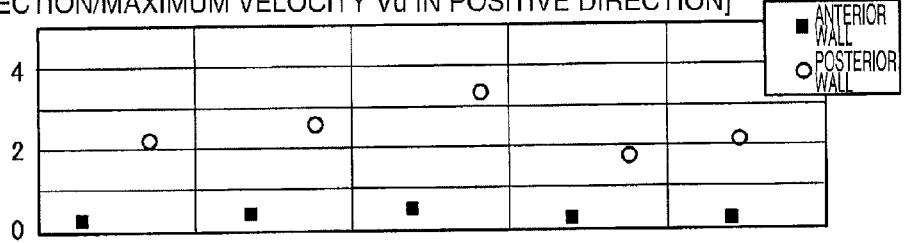
Figure 4B:
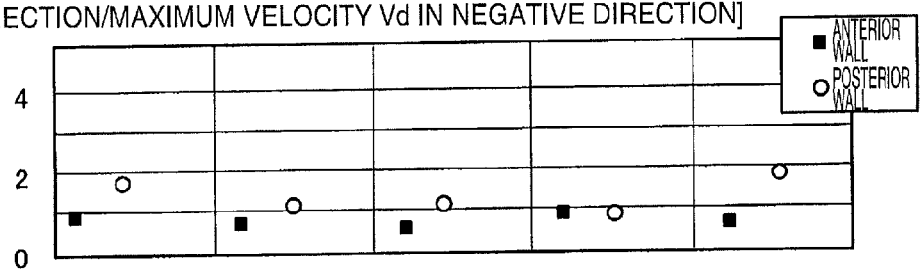

First, when viewing the artery of FIGS. 3A to 3C, as shown in FIG. 3A, in the displacement velocity waveform of the anterior arterial wall, a significant peak (the maximum displacement velocity Vu in the positive direction) appears in the positive direction due to the rapid swelling of the blood vessel during systole. However, since the blood vessel returns to the original size slowly during contraction, the peak in the negative direction (the maximum displacement velocity Vd in the negative direction) becomes smaller than the peak in the positive direction. For this reason, as shown in FIG. 3B, the first peak ratio (black square plot) for anterior arterial wall displacement has a greater value than the first peak ratio (white circular plot) of the posterior wall.

Similarly, in the displacement velocity waveform of the posterior arterial wall, a significant peak (Vd) appears in the negative direction due to the swelling of the blood vessel during systole. However, since the blood vessel returns to the original size slowly during contraction, the peak (Vu) in the positive direction becomes smaller than the peak in the negative direction. For this reason, as shown in FIG. 3C, the second peak ratio for the posterior arterial wall has a greater value than the second peak ratio for the anterior arterial wall.

Figure 4C:
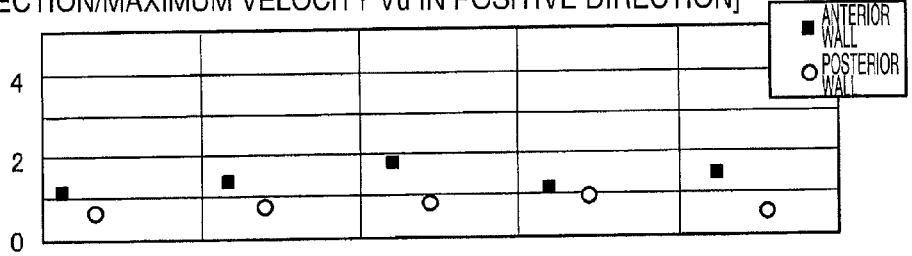

Next, when viewing the vein of FIG. 4, although the maximum peak of the displacement velocity becomes greater than the artery due to pulsation in some cases, since the tendencies in the positive direction and the negative direction are the same, as shown in FIGS. 4B and 4C, the first peak ratio and the second peak ratio become a value close to "1". That is, the first peak ratio and the second peak ratio substantially have the same value.

Accordingly, artery and vein identification is possible using the first peak ratio and the second peak ratio.

Specifically, as a feature condition representing positional change of a vascular wall of an artery, that is, a condition for identifying an artery, the following first to third feature conditions can be set.

The "first feature condition" is that the first peak ratio of the anterior wall is equal to or greater than a first feature threshold value (artery determination peak ratio threshold value). Although the first feature threshold value can be set to, for example, "2.0", the first feature threshold value may be, "2.5", "1.5", or the like. It is preferable that a value in a range of about 1.5 to 3.0 is set.

The "second feature condition" is that a value obtained by subtracting the first peak ratio of the posterior wall from the first peak ratio of the anterior wall is equal to or greater than a second feature threshold value (first peak ratio difference threshold value). Although the second feature threshold value can be set to, for example, "1.0", the second feature threshold value may be "0.8", "1.2", or the like. It is preferable that a value in a range of about 0.5 to 2.0 is set. The condition can be applied to a region of interest which is determined to be an anterior wall or an equivalent of an anterior wall and can be restated as a "feature condition for anterior wall".

The "third feature condition" is that a value obtained by subtracting the second peak ratio of the anterior wall from the second peak ratio of the posterior wall is equal to or greater than a third feature threshold value (second peak ratio difference threshold value). Although the third feature threshold value can be set to, for example, "1.0", the third feature threshold value may be "0.8", "1.2", or the like. It is preferable that a value in a range of about 0.5 to 2.0 is set. The condition can be applied to a region of interest which is determined to be a posterior wall or an equivalent of a posterior wall and can be restated as a "feature condition for posterior wall".

A comprehensive condition in which the first to third feature conditions are linked as an AND condition may be a condition for identifying an artery, or a condition that at least one condition among the first to third feature conditions is satisfied may be a condition for identifying an artery. Of course, a condition that two or more conditions among the first to third feature conditions are satisfied may be a condition for identifying an artery.

Paradoxically, as an exclusion condition for determining to be not an artery, the following first to third exclusion conditions can be set.

The "first exclusion condition" is that, for each of the anterior wall and the posterior wall, the first peak ratio and the second peak ratio satisfy an almost equal condition. Specifically, if the absolute value of the difference between both ratios is less than a predetermined first exclusion threshold value, it is determined that the equal condition is satisfied.

The "second exclusion condition" is that the first peak ratio of the anterior wall and the first peak ratio of the posterior wall satisfy an almost equal condition. Specifically, if the absolute value of the difference between both ratios is less than a second exclusion threshold value, it is determined that the equal condition is satisfied. The condition can be applied to a region of interest which is determined to be an anterior wall or an equivalent of an anterior wall and can be restated as an "exclusion condition for anterior wall".

The "third exclusion condition" is that the second peak ratio of the anterior wall and the second peak ratio of the posterior wall satisfy an almost equal condition. Specifically, if the absolute value of the difference between both ratios is less than the third exclusion threshold value, it is determined that the equal condition is satisfied. The condition may be applied to a region of interest which is determined to be a posterior wall or an equivalent to a posterior wall and can be restated as an "exclusion condition for posterior wall".

Although the first to third exclusion threshold values can be set to, for example, "1.0", the threshold values may be "0.8", "1.2", or the like.

In this embodiment, it may be possible to identify an artery and a vein on the basis of the half-width of the displacement velocity waveform.

Figure 5:
FIG. 5 is a conceptual diagram illustrating a method of identifying an artery and a vein on the basis of a half-width of a displacement velocity waveform.
Figure 5:
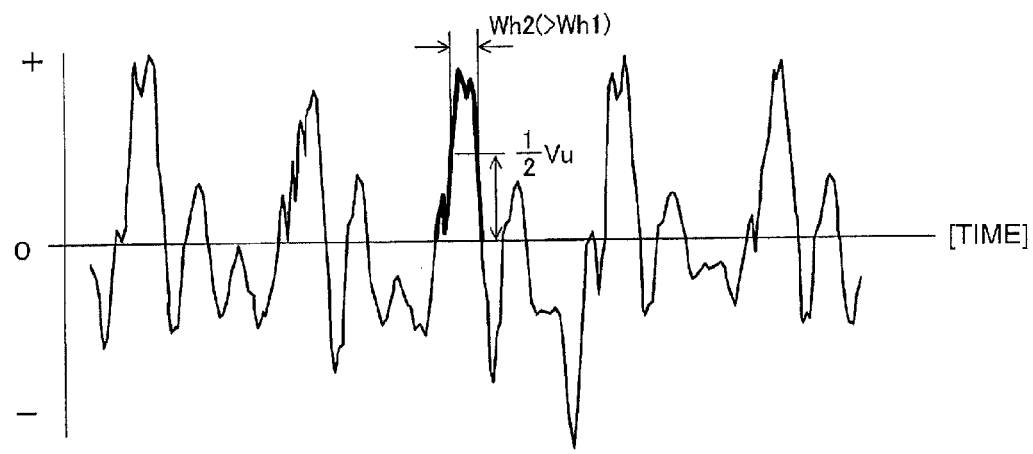

FIG. 5 is a conceptual diagram illustrating a method of identifying an artery and a vein on the basis of a half-width of a displacement velocity waveform. The upper graph shows a displacement velocity in an artery (corresponding to FIG. 3A), and the lower graph shows a displacement velocity in a vein (corresponding to FIG. 4A).

The term "the half-width of the displacement velocity waveform" refers to a width Wh in a time axis direction at half a peak value (the maximum displacement velocity Vu in the positive direction), that is, a half value in a positive direction portion (a bold solid line display portion in the drawing) of a peak waveform. When comparing a half-width Wh1 of a displacement velocity waveform of an artery with a half-width Wh2 of a displacement velocity waveform of a vein, it is understood that the half-width Wh1 of the artery becomes smaller than the half-width Wh2 of the vein. Accordingly, as a condition for identifying an artery, the following fourth feature condition can be further set.

The "fourth feature condition" is that the half-width Wh is less than a predetermined fourth feature threshold value.

Paradoxically, the following fourth exclusion condition can be set.

The "fourth exclusion condition" is that the half-width Wh is equal to or greater than the predetermined fourth feature threshold value. The "fourth exclusion condition" may be configured that the half-width Wh is equal to or greater than a predetermined fifth feature threshold value, and the fifth feature threshold value may be set to a value greater than the fourth feature threshold value.

Description of Functional Configuration

Next, a functional configuration for realizing this embodiment will be described.

Figure 6:
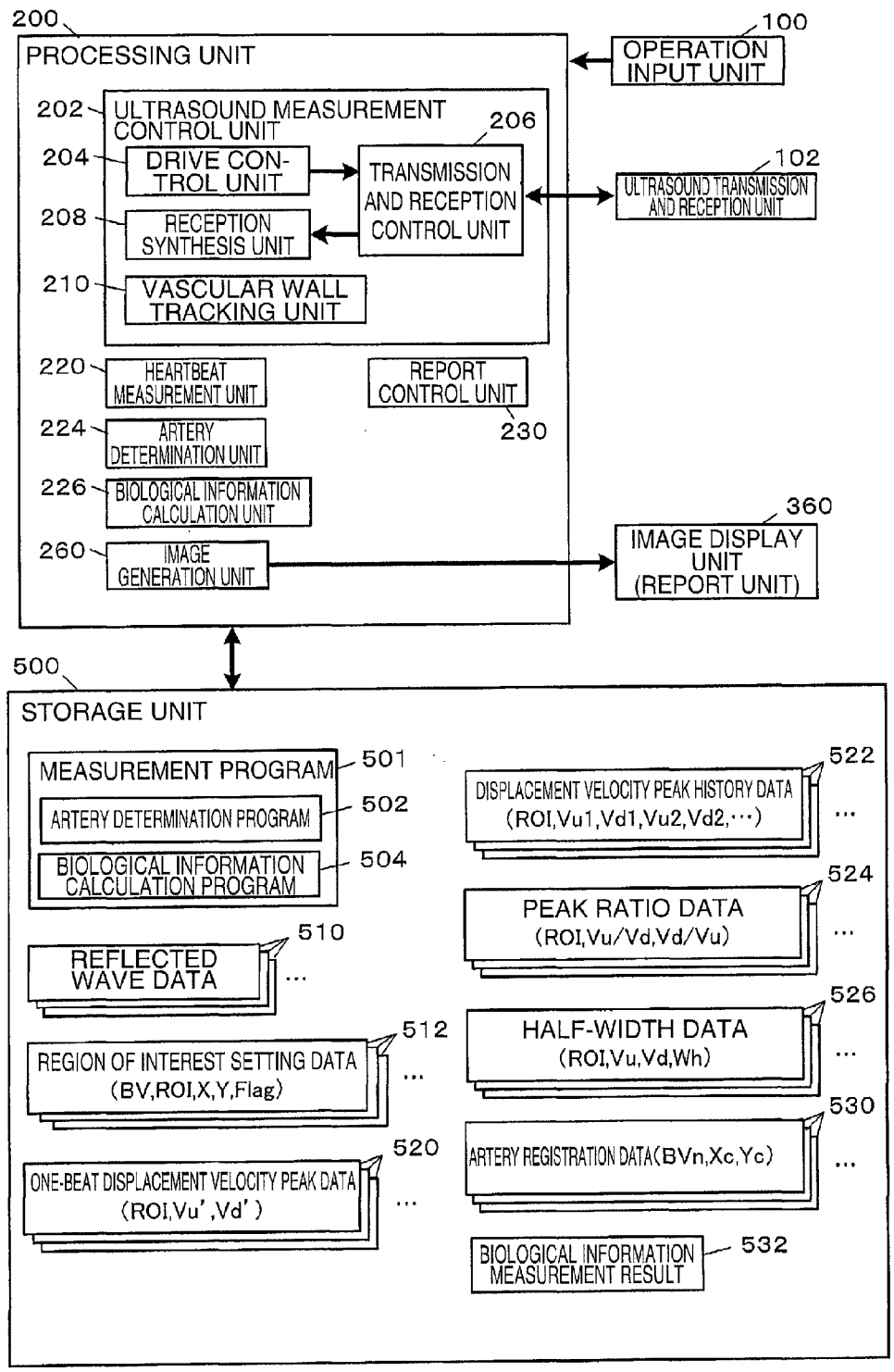
FIG. 6 is a block diagram showing a functional configuration example of a biological information measurement apparatus.

FIG. 6 is a block diagram showing a functional configuration example of the ultrasound measurement apparatus 10 of this embodiment. The ultrasound measurement apparatus 10 includes an operation input unit 100, an ultrasound transmission and reception unit 102, a processing unit 200, an image display unit 360, and a storage unit 500.

The operation input unit 100 receives various operation inputs by the operator and outputs operation input signals according to the operation inputs to the processing unit 200. The operation input unit 100 can be realized by a button switch, a lever switch, a dial switch, a track pad, a mouse, and the like. The touch panel 12 or the keyboard 14 of FIG. 1 corresponds to the operation input unit 100.

The ultrasound transmission and reception unit 102 transmits an ultrasonic wave with a pulse voltage output from the processing unit 200.

Then, the ultrasound transmission and reception unit 102 receives a reflected wave of the transmitted ultrasonic wave, converts the reflected wave to a reflected wave signal, and outputs the reflected wave signal to the processing unit 200. The ultrasound probe 16 of FIG. 1 corresponds to the ultrasound transmission and reception unit 102.

The processing unit 200 is realized by, for example, electronic components including a microprocessor, such as a CPU or a GPU, an ASIC, an IC memory, and the like. The processing unit 200 performs input/output control of data between the respective functional units and executes various kinds of arithmetic processing on the basis of predetermined programs or data, the operation input signals from the operation input unit 100, the reflected wave signal from the ultrasound transmission and reception unit 102, and the like to calculate biological information of the subject 2. The processing device 30 and the control board 31 of FIG. 1 correspond to the processing unit 200.

In this embodiment, the processing unit 200 has an ultrasound measurement control unit 202, a heartbeat measurement unit 220, an artery determination unit 224, a biological information calculation unit 226, a report control unit 230, and an image generation unit 260.

The ultrasound measurement control unit 202 has a drive control unit 204, a transmission and reception control unit 206, a reception synthesis unit 208, and a vascular wall tracking unit 210, and integrally controls ultrasound measurement. The ultrasound measurement control unit 202 can be realized by a known technique.

The drive control unit 204 controls the transmission timing of an ultrasonic pulse from the ultrasound probe 16 and outputs a transmission control signal to the transmission and reception control unit 206.

The transmission and reception control unit 206 generates a pulse voltage in accordance with the transmission control signal from the drive control unit 204 and outputs the pulse voltage to the ultrasound transmission and reception unit 102. At this time, transmission delay processing may be performed to adjust the output timing of the pulse voltage to each ultrasound transducer. Amplification or filtering processing of the reflected wave signal output from the ultrasound transmission and reception unit 102 may be performed, and the result may be output to the reception synthesis unit 208.

The reception synthesis unit 208 performs delay processing or the like as necessary to execute processing relating to so-called reception signal focusing or the like and generates reflected wave data.

The vascular wall tracking unit 210 performs processing relating to so-called "tracking" to track the position of a blood vessel (specifically, a vascular wall) in a biological tissue between the frames of ultrasound measurement on the basis of reflected wave data (reflected wave signal). For example, processing for setting a region of interest (tracking point) in reflected wave data (for example, B-mode image) as a reference, processing for tracking each region of interest between different frames, and processing for calculating displacement of each region of interest can be performed. A function of so-called known "echo tracking", "phase difference tracking", or the like is realized.

The heartbeat measurement unit 220 measures the cardiac cycle pulsation. In this embodiment, although the cardiac cycle pulsation is measured by searching the peak of reflected wave data, the cardiac cycle pulsation may be measured from variation in blood pressure acquired from an external blood pressure measurement apparatus.

The artery determination unit 224 determines whether or not a location (that is, a blood vessel) where a region of interest to be tracked is set is an artery on the basis of whether or not positional change of a region of interest set in a vascular wall obtained by the vascular wall tracking unit 210 satisfies a predetermined feature condition representing positional change of a vascular wall of an artery. The feature condition used herein may include at least one of the above-described first to fourth feature conditions, and these feature conditions may be linked as an AND condition or an OR condition.

When the positional change of the region of interest set in the vascular wall satisfies a predetermined exclusion condition, the blood vessel to be tracked can be determined to be a vein and excluded from artery determination. The exclusion condition used herein may include at least one of the above-described first to fourth exclusion conditions, and these exclusion conditions may be linked as an AND condition or an OR condition. For example, under the first exclusion condition, when the ratio of the displacement velocity in the positive direction to the displacement velocity in the negative direction and the ratio of the displacement velocity in the negative direction to the displacement velocity in the positive direction satisfy a predetermined almost equal condition, the artery determination unit 224 can determine that the blood vessel to be tracked is not an artery.

The biological information calculation unit 226 calculates intended biological information (in this embodiment, IMT) from reflected wave data of the artery determined by the artery determination unit 224.

As a method of calculating biological information, a known technique may be appropriately used, and the biological information to be calculated is not limited to the IMT, and other kinds of information, such as a vascular diameter or a blood pressure, may be calculated. For example, in case of the IMT, a lumen-intima interface and a media-adventitia interface may be determined, and the IMT may be calculated from the distance between these interfaces. Alternatively, a vascular diameter may be calculated, and a blood pressure may be calculated from a blood pressure calculation formula using a stiffness parameter β. Note that other measurement apparatuses (for example, a sphygmomanometer and the like) may be added to the configuration shown in FIG. 1 depending on the type of biological information to be calculated.

The report control unit 230 performs control to report the determination result of the artery determination unit 224. Specifically, for example, display control is performed such that the determination state on whether or not the blood vessel to be tracked is an artery is displayed on the image display unit 360, and when the determination result by the artery determination unit 224 is obtained, the determination result is displayed on the image display unit 360. When there are a plurality of regions of interest, display control regarding whether or not there is a region of interest which is determined to be an artery may be performed. When a given time is required to calculate biological information, the display of the fact that there is a region of interest which is determined to be an artery also becomes display which alerts to keep the ultrasound probe 16 stationary. Note that "report" is not limited to display, and sound output, output of a predetermined notification signal, or the like may be used.

The image generation unit 260 generates an image for displaying various operation screens necessary for ultrasound measurement or biological information measurement or the measurement results and outputs the image to the image display unit 360.

The image display unit 360 displays image data input from the image generation unit 260. The touch panel 12 of FIG. 1 corresponds to the image display unit 360.

The storage unit 500 is realized by a storage medium, such as an IC memory, a hard disk, or an optical disc, and stores various programs or various kinds of data, such as data in the calculation process of the processing unit 200. In the FIG. 1, the storage medium 33 which is mounted on the control board 31 of the processing device 30 corresponds to the storage unit 500. Note that the connection of the processing unit 200 and the storage unit 500 is not limited to connection by an internal bus circuit in the apparatus, and may be realized by a communication line, such as a LAN (Local Area Network) or Internet. In this case, the storage unit 500 may be realized by an external storage device different from the ultrasound measurement apparatus 10.

The storage unit 500 stores a measurement program 501, reflected wave data 510, region of interest setting data 512, one-beat displacement velocity peak data 520, displacement velocity peak history data 522, peak ratio data 524, half-width data 526, artery registration data 530, and a biological information measurement result 532. Of course, frame identification information, various flags, a counter value for clocking, and the like are further appropriately stored.

The processing unit 200 reads and executes the measurement program 501 to realize the functions of the ultrasound measurement control unit 202, the heartbeat measurement unit 220, the artery determination unit 224, the biological information calculation unit 226, the report control unit 230, the image generation unit 260, and the like. Note that, when these functional units are realized by hardware, such as an electronic circuit, a part of a program for realizing the function may be omitted. For example, if the artery determination unit 224 is realized by an LSI (Large Scale Integration) or the like, an artery determination program 502 may be omitted.

Reflected wave data 510 is reflected wave data obtained by ultrasound measurement and generated for each frame by the ultrasound measurement control unit 202.

Region of interest setting data 512 is definition data of a region of interest associated with an artery candidate.

One piece of region of interest setting data 512 includes blood vessel identification information (BV) of a corresponding artery candidate, region of interest identification information (ROI), a coordinate value (X,Y) which defines the reference point of a region of interest, and a flag for anterior wall/posterior wall identification (anterior wall=1, posterior wall=0).

One-beat displacement velocity peak data 520 is prepared for each region of interest, and stores region of interest identification information (ROI), a displacement velocity (Vu') in a positive direction, and a displacement velocity (Vd') in a negative direction. Specifically, while ultrasound measurement for one beat of the cardiac cycle is being executed, if the latest displacement velocity in the positive direction is greater than the currently stored value (Vu'), data is updated by the latest displacement velocity in the positive direction.

Then, the peak value which is recorded when measurement for one beat of the cardiac cycle is completed becomes the maximum displacement velocity Vu in the positive direction in the cardiac cycle.

The same applies to the negative direction, and the peak value which is recorded when measurement for one beat of the cardiac cycle is completed becomes the maximum displacement velocity Vd in the negative direction in the cardiac cycle.

Displacement velocity peak history data 522 is provided for each region of interest (ROI), combinations of the maximum displacement velocity Vu in the positive direction and the maximum displacement velocity Vd in the negative direction are stored in time series (Vu1, Vd1, Vu2, Vd2, . . . ). Specifically, for each beat of the cardiac cycle, the displacement velocity (Vu') in the positive direction and the displacement velocity (Vd') in the negative direction stored in one-beat displacement velocity peak data 520 at this time are stored in combination as the maximum displacement velocity Vu in the positive direction and the maximum displacement velocity Vd in the negative direction in the cardiac cycle. The combinations are stored in time series and historically.

Peak ratio data 524 is provided for each region of interest, and a first peak ratio (Vu/Vd) and a second peak ratio (Vd/Vu) in a corresponding region of interest are stored. In calculation of the peak ratio, the average value of the maximum displacement velocity Vu in the positive direction and the average value of the maximum displacement velocity Vd in the negative direction for a predetermined cardiac cycle stored in displacement velocity peak history data 522 are used.

Half-width data 526 is provided for each region of interest, and stores the maximum displacement velocity (Vu) in the positive direction and the maximum displacement velocity (Vd) in the negative direction used for peak ratio calculation, and half-width (Wh).

Artery registration data 530 is definition data of the determined artery. For example, blood vessel identification information (BV) and a blood vessel center coordinate (Xc,Yc) are stored.

The biological information measurement result 532 stores the calculated biological information in time series.

Description of Flow of Processing

Next, the operation of the ultrasound measurement apparatus 10 will be described.

It is assumed that ultrasound measurement already starts, and reflected wave data 510 associated with frame identification information of measurement is stored sequentially in the storage unit 500.

Two regions of interest which are considered as an anterior wall and a posterior wall are set using reflected wave data 510 for each blood vessel as an artery candidate, and region of interest setting data 512 which defines the set region of interest is created in the storage unit 500. Note that a region of interest may be manually set by the operator or may be automatically set by predetermined signal processing.

Figure 7:
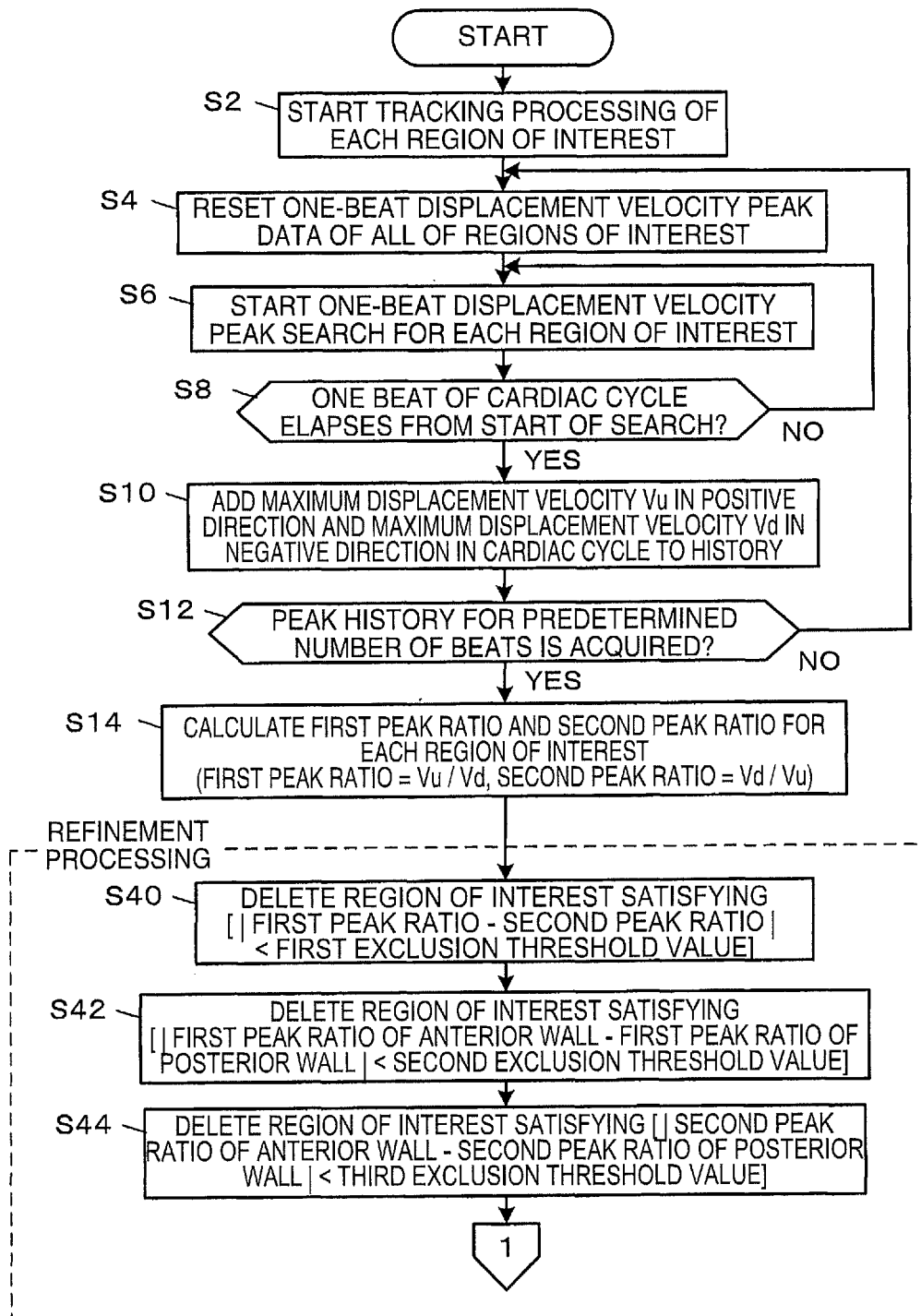
FIG. 7 is a flowchart illustrating the flow of processing in an ultrasound measurement apparatus.
Figure 8:
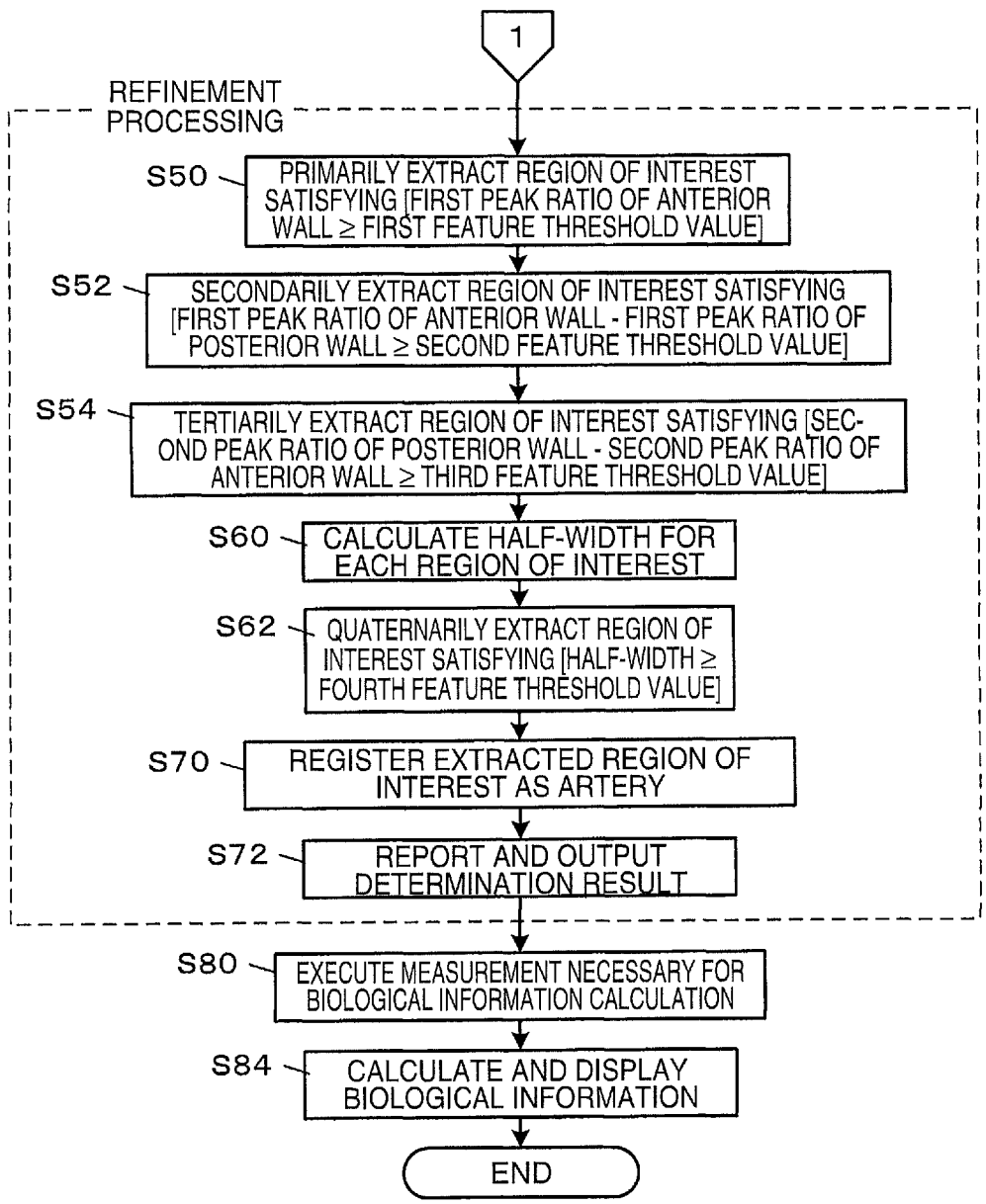
FIG. 8 is a flowchart subsequent to FIG. 7.

FIGS. 7 to 8 are flowcharts illustrating the flow of processing in the ultrasound measurement apparatus 10 of this embodiment.

First, the processing unit 200 starts tracking processing of each region of interest set at a location which is considered as a vascular wall (Step S2), and initializes the value of each of the displacement velocity Vu' in the positive direction and the displacement velocity Vd' in the negative direction included in one-beat displacement velocity peak data 520 of each region of interest to a predetermined initial value (Step S4).

Then, a one-beat displacement velocity peak search starts for each region of interest (Step S6). For example, the displacement velocity in the positive direction obtained from reflected wave data of the latest frame is compared with the displacement velocity Vu' in the positive direction of one-beat displacement velocity peak data 520, and if the former is greater, the displacement velocity Vu' in the positive direction is updated to the obtained displacement velocity. Similarly, the displacement velocity in the negative direction obtained from reflected wave data of the latest frame is compared with the displacement velocity Vd' in the negative direction stored in one-beat displacement velocity peak data 520, and if the former is greater, the displacement velocity Vd' in the negative direction is updated to the obtained displacement velocity.

If one beat of the cardiac cycle elapses from the start of the peak search (YES of Step S8), the processing unit 200 stores the displacement velocity Vu' in the positive direction and the displacement velocity Vd' in the negative direction stored in one-beat displacement velocity peak data 520 at this time in displacement velocity peak history data 522 associated with region of interest identification information (ROI) as the maximum displacement velocity Vu in the positive direction and the maximum displacement velocity Vd in the negative direction in the cardiac cycle (Step S10). With this, a displacement velocity peak history for one beat of the cardiac cycle is obtained.

The processing unit 200 repeats Steps S4 to S10 (NO of Step S12).

Then, if a peak history for a predetermined number of heartbeats (for example, four to five beats) is obtained (YES of Step S12), next, the first peak ratio and the second peak ratio are calculated for each region of interest (Step S14).

Specifically, the average value of the maximum displacement velocity Vu in the positive direction and the average value of the maximum displacement velocity Vd in the negative direction in a plurality of pulsation periods stored in displacement velocity peak history data 522 are calculated.

Then, these are regarded as the maximum displacement velocity Vu in the positive direction and the maximum displacement velocity Vd in the negative direction in the region of interest, the first peak ratio (Vu/Vd) is calculated, and the calculated first peak ratio is stored in the storage unit 500 as peak ratio data 524 in association with the identification information (ROI) of the region of interest.

Similarly, the average value of the maximum displacement velocity Vu in the positive direction and the average value of the maximum displacement velocity Vd in the negative direction are calculated, and the second peak ratio (Vd/Vu) is calculated for each region of interest and stored in peak ratio data 524. Instead of the "average value" used in this step, other statistical values, such as a median value, may be used. Alternatively, the maximum value of the maximum displacement velocity Vu in the positive direction and the maximum value of the maximum displacement velocity Vd in the negative direction stored in displacement velocity peak history data 522 may be used.

If the first peak ratio and the second peak ratio are obtained, next, the processing unit 200 performs refinement for a region corresponding to an artery from a region of interest (refinement processing: S40 to S70).

As a first stage of refinement, the processing unit 200 deletes region of interest setting data 512 of a region of interest satisfying an exclusion condition (Steps S40 to S44).

Specifically, a region of interest in which the absolute value of a value obtained by subtracting the second peak ratio from the first peak ratio is less than the first exclusion threshold value is regarded as "a region of interest in which the first peak ratio and the second peak ratio satisfy an equal condition", and deletes corresponding region of interest setting data 512 (Step S40). That is, a region of interest satisfying the above-described first exclusion condition is excluded from the candidates for artery determination.

Next, the processing unit 200 deletes region of interest setting data 512 of a region of interest in which the absolute value of a value obtained by subtracting the first peak ratio of the posterior wall from the first peak ratio of the anterior wall of the same region of interest is less than the first exclusion threshold value (Step S42). That is, a region of interest satisfying the above-described second exclusion condition is excluded from the candidates for artery determination.

Next, the processing unit 200 deletes region of interest setting data 512 of a region of interest in which the absolute value of a value obtained by subtracting the second peak ratio of the posterior wall from the second peak ratio of the anterior wall of the same region of interest is less than the third exclusion threshold value (Step S44). That is, a region of interest satisfying the above-described third exclusion condition is excluded from the candidates for artery determination.

Referring to FIG. 8, next, the processing unit 200 extracts a region of interest satisfying the feature condition as a second stage of refinement (Steps S50 to S60).

Specifically, a region of interest in which "the first peak ratio of the anterior wall is equal to or greater than the first feature threshold value" is regarded as a region of interest satisfying the first feature condition and primarily extracted (Step S50).

Next, a region of interest in which "a value obtained by subtracting the first peak ratio of the posterior wall from the first peak ratio of the anterior wall is equal to or greater than the second feature threshold value" among the primarily extracted regions of interest is regarded as a region of interest satisfying the second feature condition and secondarily extracted (Step S52).

Next, a region of interest in which "a value obtained by subtracting the second peak ratio of the posterior wall from the second peak ratio of the anterior wall is equal to or greater than the second feature threshold value" among the secondarily extracted regions of interest is regarded as a region of interest satisfying the third feature condition and tertiarily extracted (Step S54).

Subsequently, as a third stage of refinement, the processing unit 200 calculates the half-width Wh (see FIG. 5) on the tertiarily extracted region of interests (Step S60), and quaternarily extracts a region of interest in which "the half-width Wh is equal to or greater than the fourth feature threshold value" (Step S62).

Then, the extracted region of interest is regarded as an artery, and the identification information of the region of interest is registered in the artery registration data 530 (Step S70). With this, the identification of an artery and a vein is completed, and the center position of the artery is determined. The report control unit 230 performs control to report and output a determination result regarding whether or not there is a region of interest which is determined to be an artery, that is, whether or not a blood vessel to be tracked is an artery (Step S72).

Next, the processing unit 200 executes ultrasound measurement necessary for biological information calculation on the determined artery (Step S80), and calculates the biological information from the measurement result (Step S82).

According to this embodiment, it is possible to identify an artery and a vein and to automatically specify the position of an artery.

Note that the invention is not limited to the foregoing embodiment, and additions, omissions, and alterations of the constituent elements may be appropriately made.

For example, in the foregoing embodiment, although a configuration in which the first feature condition to the fourth feature condition and the first exclusion condition to the third exclusion condition are used in the process of the refinement is made, the number of feature conditions or exclusion conditions to be used or the combination of feature conditions or exclusion conditions may be appropriately changed.

Figure 9:
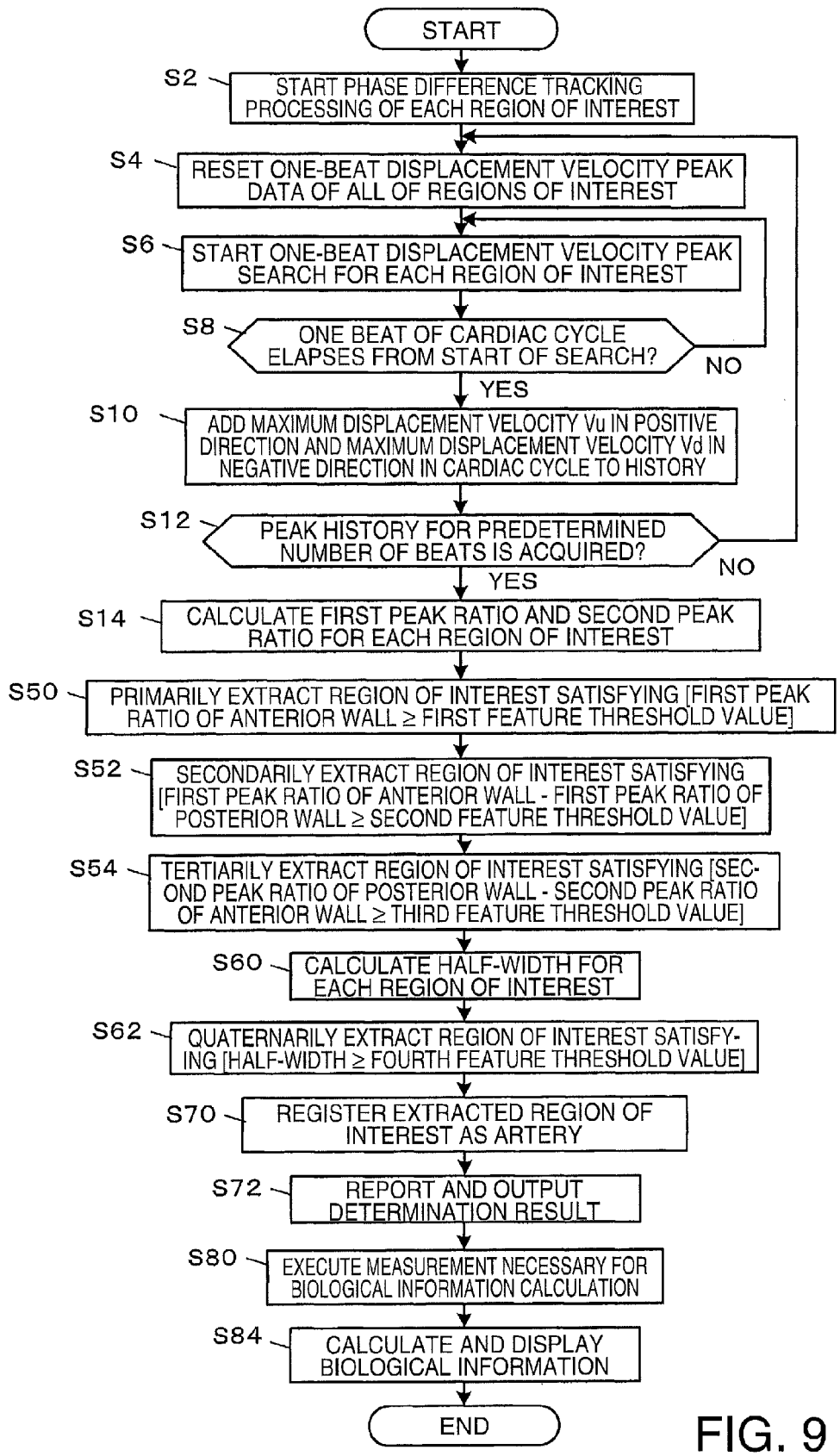
FIG. 9 is a flowchart illustrating the flow of processing of an ultrasound measurement apparatus in a first modification example.
Figure 10:
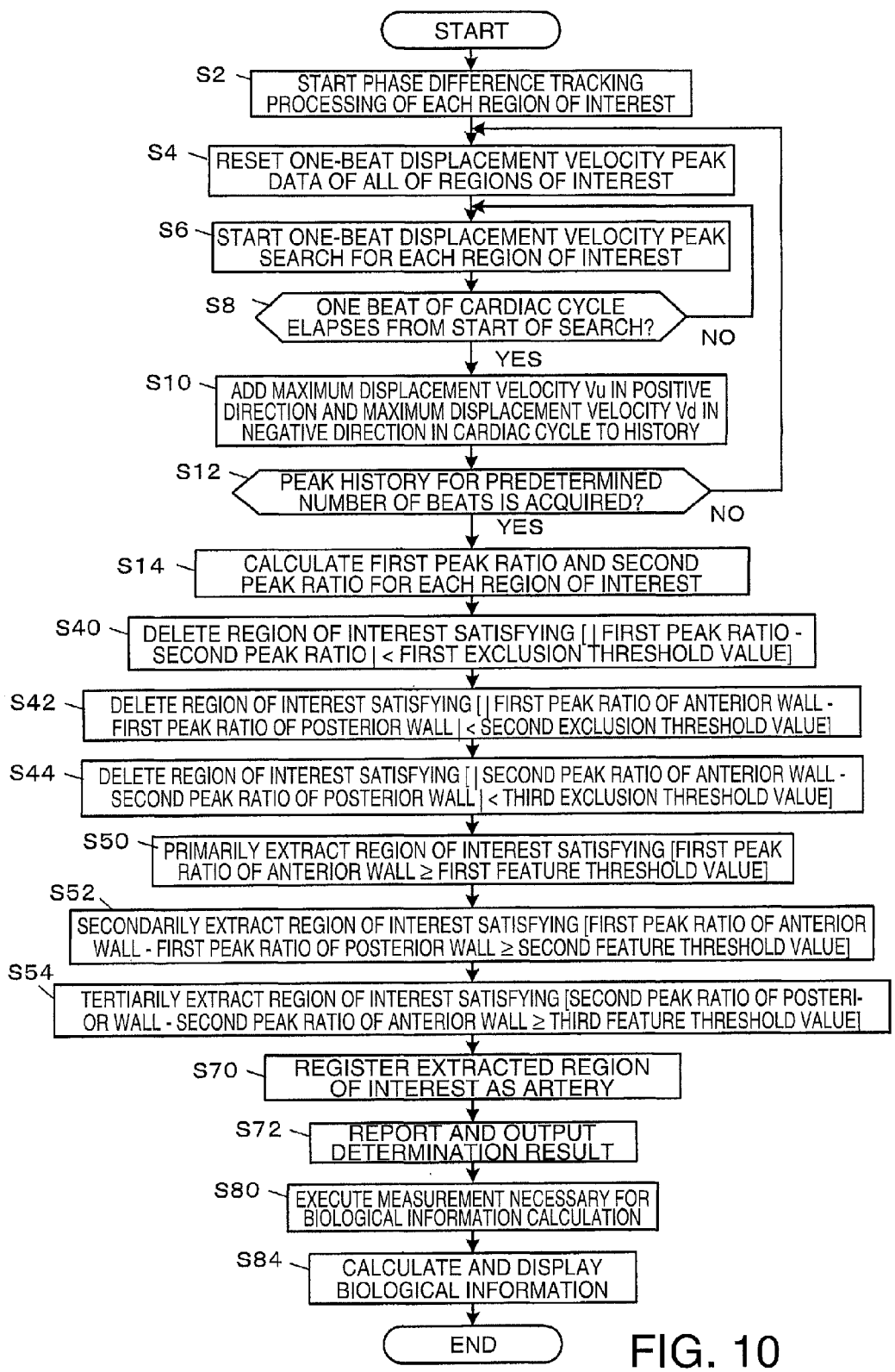
FIG. 10 is a flowchart illustrating the flow of processing of an ultrasound measurement apparatus in a second modification example.
Figure 11:
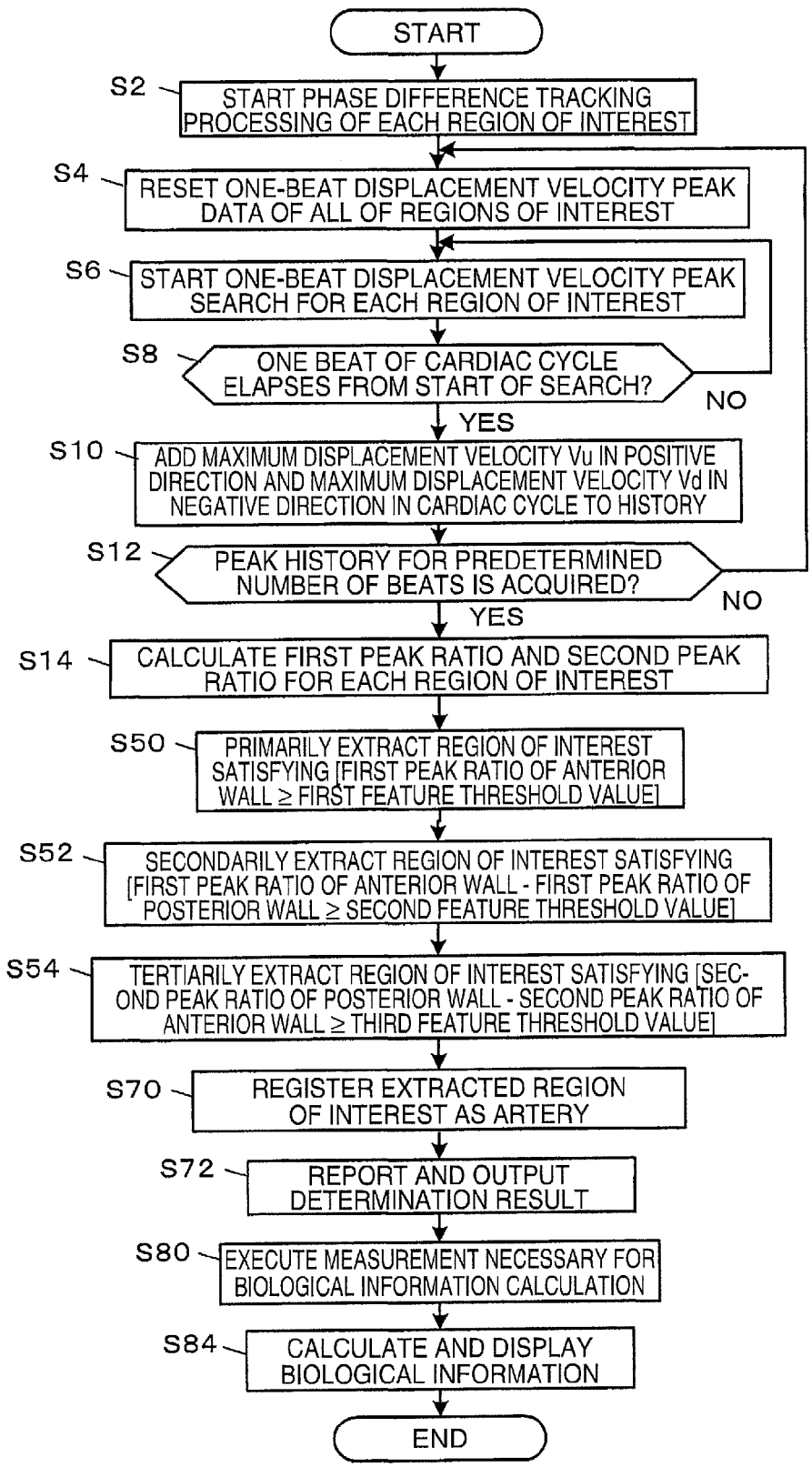
FIG. 11 is a flowchart illustrating the flow of processing of an ultrasound measurement apparatus in a third modification example.
Figure 12:
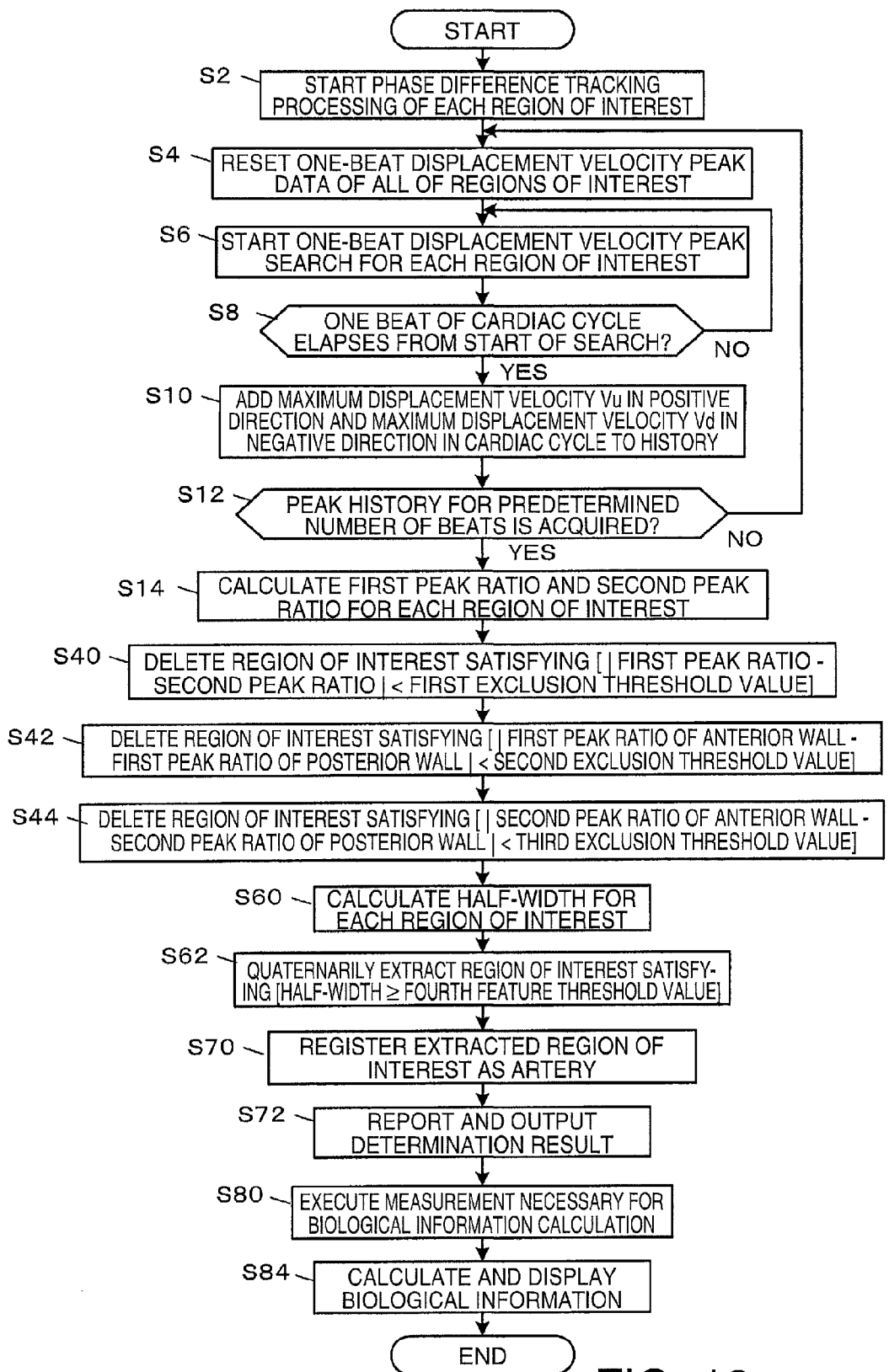
FIG. 12 is a flowchart illustrating the flow of processing of an ultrasound measurement apparatus in a fourth modification example.

Specifically, as shown in FIG. 9, all or some of Steps S40 to S44 may be deleted from the configuration of the foregoing embodiment. As shown in FIG. 10, a configuration in which all or some of Steps S60 to S62 are deleted from the configuration of the foregoing embodiment may be made, or as shown in FIG. 11, a configuration in which both of Steps S40 to S44 and Steps S60 to S62 are deleted may be made. Conversely, as shown in FIG. 12, a configuration in which Steps S50 to S54 are excluded from the foregoing embodiment may be made.

The displacement velocity in the foregoing embodiment may be appropriately replaced with a displacement acceleration.

The entire disclosure of Japanese Patent Application No. 2013-117620, filed Jun. 4, 2013, is expressly incorporated by reference herein.

What is claimed is:

1. An ultrasound measurement apparatus comprising:
a probe that is configured to transmit an ultrasonic wave to a blood vessel and receive a reflected wave from the blood vessel;
a processor that is configured to:
    track a position of a vascular wall of the blood vessel in a biological tissue on the basis of the reflected wave;
    measure a displacement velocity in a positive direction and a displacement velocity in a negative direction of the vascular wall; and
    determine whether or not the blood vessel to be tracked is an artery based on a relative relationship between the displacement velocity in the positive direction and the displacement velocity in the negative direction, and determine that the blood vessel to be tracked is the artery when the displacement velocity in the positive direction and the displacement velocity in the negative direction satisfy a predetermined condition; and
a display that displays the determination result.

2. The ultrasound measurement apparatus according to claim 1,
wherein the processor performs the determination using the ratio of the displacement velocity in the positive direction to the displacement velocity in the negative direction and the ratio of the displacement velocity in the negative direction to the displacement velocity in the positive direction.

3. An ultrasound measurement apparatus comprising:
a probe that is configured to transmit an ultrasonic wave to a blood vessel and receive a reflected wave from the blood vessel;
a processor that is configured to:
    track a position of a vascular wall of the blood vessel in a biological tissue on the basis of the reflected wave;
    measure a displacement velocity in a positive direction and a displacement velocity in a negative direction of the vascular wall; and
    determine whether or not the blood vessel to be tracked is an artery based on a relative relationship between the displacement velocity in the positive direction and the displacement velocity in the negative direction; and
a display that displays the determination result,
wherein the processor determines that the blood vessel to be tracked is not an artery when a difference between (i) a ratio of the displacement velocity in the positive direction to the displacement velocity in the negative direction and (ii) a ratio of the displacement velocity in the negative direction to the displacement velocity in the positive direction is less than a predetermined value.

4. The ultrasound measurement apparatus according to claim 1,
wherein the processor performs the determination using a first condition for an anterior vascular wall when the vascular wall is an anterior vascular wall and performs the determination using a second condition for a posterior vascular wall when the vascular wall is a posterior vascular wall.

5. The ultrasound measurement apparatus according to claim 1,
wherein the processor performs the determination using the peak waveform of a displacement velocity of the vascular wall.

6. An ultrasound measurement method for measuring biological information, the method being performed by an ultrasound measurement apparatus, the ultrasound measurement apparatus comprising a probe, a processor and display, the method comprising:
transmitting an ultrasonic wave to a blood vessel and receiving a reflected wave from the blood vessel, a step being performed by the probe,
tracking a position of a vascular wall of the blood vessel in a biological tissue on the basis of the reflected wave, a step being performed by the processor;
measure a displacement velocity in a positive direction and a displacement velocity in a negative direction of the vascular wall, a step being performed by the processor; and
determining whether or not the blood vessel to be tracked is an artery based on a relative relationship between the displacement velocity in the positive direction and the displacement velocity in the negative direction, and determining that the blood vessel to be tracked is the artery when the displacement velocity in the positive direction and the displacement velocity in the negative direction satisfy a predetermined condition, a step being performed by the processor; and
displaying the determination result, a step being performed by the display.

7. The ultrasound measurement apparatus according to claim 1, wherein the processor determines that the blood vessel to be tracked is the artery when a ratio of the displacement velocity in the positive direction to the displacement velocity in the negative direction is equal to or more than a predetermined value.

8. The ultrasound measurement method according to claim 6, wherein the processor determines that the blood vessel to be tracked is the artery when a ratio of the displacement velocity in the positive direction to the displacement velocity in the negative direction is equal to or more than a predetermined value.

* * * * *